United States Patent [19]

Winn et al.

[11] 4,007,207
[45] Feb. 8, 1977

[54] ALKYL SUBSTITUTED-4-OXO-CYCLOPENTA BENZOPYRANS

[75] Inventors: Martin Winn, Deerfield, Ill.; Raj Kumar Razdan, Belmont, Mass.; Haldean Cloyce Dalzell, Weston, Mass.; Joyce Ruth Krei, Glenview, Ill.

[73] Assignee: Sharps Associates, Cambridge, Mass.

[22] Filed: July 9, 1975

[21] Appl. No.: 594,534

Related U.S. Application Data

[62] Division of Ser. No. 392,635, Aug. 29, 1973, Pat. No. 3,929,835.

[52] U.S. Cl. .................. 260/343.2 R; 424/279; 260/345.3; 260/621 K
[51] Int. Cl.² ............................. C07D 311/78
[58] Field of Search ............... 260/343.2 R

[56] References Cited

UNITED STATES PATENTS 3,639,426   2/1972   Razdan et al. .................. 260/345.3

*Primary Examiner*—John M. Ford
*Attorney, Agent, or Firm*—Merriam, Marshall, Shapiro & Klose

[57] ABSTRACT

1,2,3,4-Tetrahydrocyclopenta[c][1]benzopyrans of the formulae

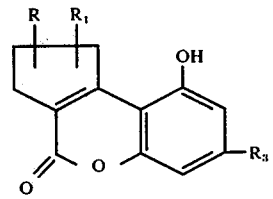

and

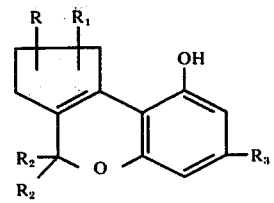

wherein R is a lower alkyl group having 1 to 5 carbons, $R_1$ is hydrogen or a lower alkyl group having 1 to 5 carbons, $R_2$ is a lower alkyl group and $R_3$ is an alkyl group having 1 to 20 carbon atoms, a phenyl-lower alkyl group or a cycloalkyl-lower alkyl group. The compounds have anti-hypertensive, antidepressant, analgesic, anticonvulsant, anti-anxiety, sedative-hypnotic and tranquilizing activity in animals.

6 Claims, No Drawings

ALKYL SUBSTITUTED-4-OXO-CYCLOPENTA BENZOPYRANS

This is a division of application Ser. No. 392,635, filed Aug. 29, 1973, now U.S. Pat. No. 3,929,835.

This invention relates to novel chemical compounds and processes of producing the same. More particularly, this invention is concerned with novel benzopyrans and the use of such compounds, particularly those having pharmacological activity.

According to one aspect of the subject invention there is provided novel 1,2,3,4tetrahydrocyclopenta[c][1] benzopyrans of the formula

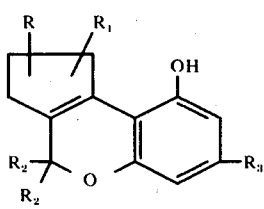

Formula 1 wherein R is a lower alkyl having 1 to 5 carbons and $R_1$ is hydrogen or a lower alkyl group having 1 to 5 carbons, and when R and $R_1$ are both lower alkyl such groups can be on the same or different carbon atoms in the cyclopenta or C-ring moiety, $R_2$ is a lower alkyl group and $R_3$ is an alkyl group having 1 to 20 carbon atoms, a phenyl-lower alkyl group or a cycloalkyl-lower alkyl group, and novel intermediates useful in making such compounds. When R and $R_1$ are both in the 1-position on the ring system, generally only one of such groups will be alkyl and the other will be hydrogen.

As used herein, the term lower-alkyl means saturated, monovalent aliphatic-radicals, including straight and branched-chain radicals of from one to six carbon atoms, as illustrated by, but not limited to methyl, ethyl, propyl, isopropyl, butyl, sec.-butyl, amyl, hexyl and the like.

As used herein, the term alkyl means saturated, monovalent aliphatic radicals, including straight and branched chain radicals of from one to twenty carbon atoms, as illustrated by, but not limited to methyl, n-amyl, n-hexyl, 2-heptyl, n-heptyl, 3-methyl-2-octyl, n-octyl, 2-nonyl, 2-tetracdecyl, n-hexadecyl, 2-eicosanyl, and the like.

As used herein, the term cycloalkyl means cyclic, saturated aliphatic-radicals of from three to eight carbon atoms, as illustrated by, but not limited to cyclopropyl, cyclobutyl, 2-methylcyclobutyl, cyclohexyl, 4-methylcyclohexyl, cyclooctyl, and the like.

As used herein, the term phenyl-lower alkyl, means a monovalent radical consisting of a phenyl nucleus bonded to the rest of the molecule, respectively, through a divalent lower-alkylene radical of from one to six carbon atoms as illustrated by, but not limited to methylene, 1,1-ethylene, 1,2-ethylene, 1,3-propylene, 1,2-propylene, 1,4-butylene, and the like. Here and elsewhere throughout this specification, it will be understood the benzene or phenyl ring can bear any number and kind of substituents such as would occur to the man skilled in organic chemistry. Solely for illustration, and without limitation, such substituents include lower-alkyl, lower-alkoxy, halo (chloro, bromo, iodo or fluoro), nitro, lower-alkylmercapto, and the like.

The compounds of Formula 1 can be prepared by reacting a 5-substituted resorcinol of Formula 2

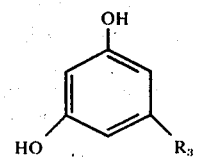

Formula 2 wherein $R_3$ has the previously assigned significance, with a 2-carbo-lower alkoxy-cyclopentanone of Formula 3

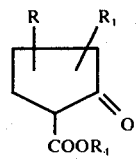

Formula 3 wherein $R_4$ represents a lower alkyl group, to produce a 4-oxo-1,2,3,4-tetrahydrocyclopenta[c][1]benzopyran of Formula 4

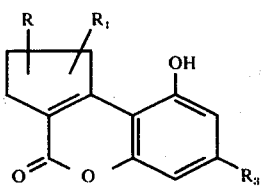

Formula 4 which can then be reacted with a lower alkyl magnesium halide to produce a compound of Formula 5

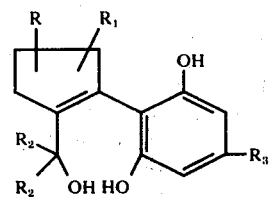

Formula 5 which is then reacted with an acid such as hydrochloric acid or p-toluene sulfonic acid to dehydrate it to produce a 4,4-dialkyl-9-hydroxy-7-$R_3$-1,2,3,4-tetrahydrocyclopenta [c] [1]benzopyran of Formula 1, wherein in Formulas 2 to 5 the substituents and symbols have the meanings assigned as with respect to Formula 1.

Some of the 5-substituted resorcinols which can be used in the process are 5-(3-methyl-2-octyl) resorcinol, 5-pentylresorcinol, 5-benzylresorcinol, 5-(3-phenylpropyl) resorcinol, 5-[2-(p-fluorophenyl)ethyl]resorcinol. 5-cyclopentylmethyl resorcinol and 5-(3-cyclohexylpropyl) resorcinol. The resorcinol starting materials are disclosed in the chemical literature and many are commercially available.

Some of the 2-carbo-lower alkoxy-cyclopentanone starting materials of Formula 3 which can be used in the process are 2-carbethoxy-4,4-dimethyl-cyclopentanone, 2-carboethoxy-5-methyl-cyclopentanone, 2-carboethoxy-4-methyl cyclopentanone and 2-carboethoxy-5-ethyl cyclopentanone. Some of the starting materials which can be used are disclosed in J. Org.

Chem. 29, 2782 (1964); 33, 4067 (1968) and 35, 3204 (1970) and others can be prepared by following the procedures disclosed in this and other chemical literature.

The first step of the process in which the 5-substituted resorcinol is reacted with a 2-carbo-lower alkoxy cyclopentanone of Formula 3 is readily effected by bringing the reactants together in a suitable liquid reaction medium in the presence of an acid catalyst. Hydrochloric acid dissolved in ethanol is suitable for conducting the reaction. The reaction can be carried out also in a mixture of concentrated sulfuric acid and phosphorous oxychloride, or in phosphorus oxychloride either alone or in an organic solvent, for example benzene or toluene. The product can be recovered from the reaction mixture by conventional means.

Some of the products produced by the described reaction which come within the scope of Formula 4 are 1-methyl-4-oxo-9-hydroxy-7-(3-methyl-2-octyl)-1,2,3,4-tetrahydrocyclopenta[c] [1]benzopyran, 2-methyl-4-oxo-9-hydroxy-7-(3-methyl-2-octyl)-1,2,3,4-tetrahydrocyclopenta [c] [1]benzopyran, 9-hydroxy-7-(3-methyl-2-octyl)-2,2-dimethyl-4-oxo-1,2,3,4-tetrahydrocyclopenta [c] [1]benzopyran, 1-ethyl-4-oxo-9-hydroxy-7-(3-methyl-2-octyl)-1,2,3,4-tetrahydrocyclopenta[c] [1]benzopyran, 1-methyl-4-oxo-9-hydroxy-7-n-pentyl-1,2,3,4-tetrahydrocyclopenta[c] [1]benzopyran, 2-methyl-4-oxo-9-hydroxy-7-n-pentyl-1,2,3,4-tetrahydrocyclopenta[c] [1]benzopyran, 1-methyl-4-oxo-9-hydroxy-7-(3-p-fluorophenylpropyl)-1,2,3,4-tetrahydrocyclopenta[c] [1] benzopyran, and 2-methyl-4-oxo-9-hydroxy-7 -(2-cyclohexylethyl)-1,2,3,4-tetrahydrocyclopenta[c] [1]benzopyran.

The compounds of Formula 4 can be converted to the compounds of Formula 5 by reacting a compound of Formula 4 with an alkyl magnesium halide such as methyl magnesium chloride, ethyl magnesium iodide or propyl magnesium chloride. The reaction can be effected by bringing the reactants together in a suitable inert liquid reaction medium such as diethyl ether, dibutyl ether, tetrahydrofuran, anisole and pyridine. The reaction proceeds rapidly at reflux temperature. Although the desired product of Formula 5 can be isolated from the reaction mixture by standard methods after the reaction is terminated, it is generally not advantageous to isolate the triol. Instead, the triol of Formula 5 can be treated, without isolation, with an acid to convert it to a compound of Formula 1.

Some of the compounds of Formula 1 which can be produced as described are 9-hydroxy-7-(3-methyl-2-octyl)-1,4,4-trimethyl-1,2,3,4-tetrahydrocyclopenta [c] [1]benzopyran, 9-hydroxy-7-(3-methyl-2-octyl)-2,4,4-trimethyl-1,2,3,4-tetrahydrocyclopenta[c] [1]benzopyran, 9-hydroxy-7-(3-methyl-2-octyl)-2,2,4,4-tetramethyl-1,2,3,4-tetrahydrocyclopenta[c] [1]benzopyran, 1-ethyl-4,4-dimethyl-9-hydroxy-7-(3-methyl-2-octyl)-1,2,3,4-tetrahydrocyclopenta[c] [1]benzopyran, 9-hydroxy-7-n-pentyl-1,4,4-trimethyl-1,2,3,4-tetrahydrocyclopenta[c] [1]benzopyran, 9-hydroxy-7-n-pentyl-2,4,4-trimethyl-1,2,3,4-tetrahydrocyclopenta[c] [1]benzopyran, 9-hydroxy-7-(3-p-fluorophenylpropyl)-1,4,4-trimethyl-1,2,3,4-tetrahydrocyclopenta[c] [1]benzopyran, and 9-hydroxy-7-(2-cyclohexylethyl)-2,4,4-trimethyl-1,2,3,4-tetrahydrocyclopenta [c] [1]benzopyran.

The compounds of this invention have antihypertensive, antidepressant, analgesic, anticonvulsant, tranquilizing and/or anti-anxiety and sedative-hypnotic activity in animals and such activities indicates potential human use for the compounds as drugs.

The pharmacological activity for the compounds having the nuclear alkyl substitutents in the C-ring of this invention is surprisingly different from the activity of the prior art related compound 4,4-dimethyl-9-hydroxy-7-(3-methyl-2-octyl)-1,2,3,4-tetrahydrocyclopenta[c] [1]benzopyran (SP-7) disclosed in U.S. Pat. No. 3,639,426 issued Feb. 1, 1972 which does not have an alkyl group in the C-ring. This will be seen from the following summaries of the pharmacological activity of SP-7 and specific compounds provided by this invention. The data reported in the summaries was obtained using test procedures reported in the literature as follows:

1. Antihypertensive test using hypertensive rats: Tabei et al., Clinical Pharmacology and Therapeutics, 11, No. 2, p. 269 (1970).

2. Mouse odified DOPA potentiation test for antidepressant activity. Everett, G. M., Proc. First Internat. Sympos. Antidepressant Drugs, Excerpta Med. Int. Cong. Ser. No. 122, 1966.

3. Audiogenic seizure test for anticonvulsant activity: Plotnikoff, N. P., J. Pharmacol. Exp. Therap. 119, 294 (1957).

4. Mouse fighting test for tranquilizing activity: Tedeschi, R. E. et al., J. Pharmacol. Exp. Therap., 125, 28 (1959) with modifications; response to footshock measured.

5. Acetic acid induced writhing test for analgesic activity: Brit. J. Pharmacol, 22, 296 (1964).

6. Rat tail flick test for analgesic activity: J. Pharmacol. Exper. Therap., 72, 74 (1941).

7. Hot plate test for analgesic activity: J. Pharmacol. Exper. Therap., 80, 300 (1944).

8. Sedative-hypnotic test: Jewett and Norton, Experimental Neurology, 15, 463-474 (1966), with modifications.

SP-7 administered orally in a dose of 10 mg./kg., reduced the systolic blood pressure of genetically hypertensive rats. In an oral dose of 10 mg./kg., it showed marked activity in the mouse modified DOPA potentiation test. In the audiogenic seizure test, SP-7 in oral doses of 10 and 30 mg./kg., protected 25% and 65% of the mice, respectively, from the convulsions. At oral doses of 5 and 10 mg./kg., SP-7 caused 56% and 65% reductions in fighting behavior, respectively, in the mouse fighting test. SP-7 had moderate activity in the hot plate ($ED_{50}$ = 45.1 mg./kg., p.o.) and the acetic acid induced writhing test in mice ($ED_{50}$ = 25.3 mg./kg., p.o.).

SP-7 at an oral dose of 0.5 mg./kg., caused an increase of 59 minutes in total sleep time in EEG (sedative-hypnotic) studies in cats. This increase was a result of an increase of 32 minutes in the slow wave stage of sleep, no change in the spindle sleep, and an increase of 27 minutes in the rapid eye movement (REM) stage. At an oral dose of 1.0 mg./kg., SP-7 caused an increase of 65 minutes in total sleep time. This increase was a result of an increase of 65 minutes in the slow wave stage of sleep, a decrease of 12 minutes in the spindle stage, and an increase of 12 minutes in the REM stage of sleep.

9-Hydroxy-7-(3-methyl-2-octyl)-2,2,4,4-tetramethyl-1,2,3,4-tetrahydrocyclopenta[c] [1]benzopyran (SPA-4) was not tested in genetically hypertenisve rats. At an oral dose of 10 mg./kg., it showed marked activity in the mouse modified DOPA potentiation test. In the audiogenic seizure test, SPA-4 in an oral dose of 30 mg./kg., protected 20% of the mice from the convulsions. At an oral dose of 10 mg./kg., SPA-4 caused a 56% reduction in fighting behavior in the mouse fighting test. SPA-4 had no analgesic activity at the doses employed. SPA-4 is useful as an antidepressant or an anti-anxiety agent.

9-Hydroxy-7-(3-methyl-2-octyl)-2,4,4-trimethyl-1,2,3,4-tetrahydrocyclopenta[c] [1]benzopyran (SPA-47) administered orally at doses of 0.3 and 1.0 mg./kg., showed no reduction in the systolic blood pressure of genetically hypertensive rats. At an oral dose of 20 mg./kg., it showed marked activity in the mouse modified DOPA potentiation test. In the audiogenic seizure test, SPA-47 at an oral dose of 30 mg./kg., afforded no protection to the mice from the convulsions. At an oral dose of 10 mg./kg., SPA-47 caused a 19% reduction in fighting behavior in the mouse fighting test. SPA-47 had moderate activity in the acetic acid induced writhing test in mice ($ED_{50}$, 22.6 mg./kg., p.o.) SPA-47 is useful as an antidepressant or analgesic agent.

9-Hydroxy-7-(3-methyl-2-octyl)-1,4,4-trimethyl-1,2,3,4-tetrahydrocyclopenta[c] [1]benzopyran (SPA-90) administered orally at doses of 1 and 10 mg./kg., reduced the systolic blood pressure of genetically hypertensive rats. In oral doses of 5, 10 and 20 mg./kg., it was essentially inactive in the mouse modified DOPA potentiation test. In the audiongenic seizure test, SPA-90 in oral doses of 10 and 30 mg./kg., protected 80 % and 100% of the mice, respectively, from the convulsions. At an oral dose of 10 mg./kg., SPA-90 caused an 87% reduction in fighting behavior in the mouse fighting test. SPA-90 had marked activity in the acetic acid induced writhing test in mice ($ED_{50}$, 13.3 mg./kg., p.o.). SPA-90 at an oral dose of 0.5 mg./kg., caused an increase of 58 minutes in total sleep time in EEG (sedative-hypnotic) studies in cats. This increase was a result of an increase of 38 minutes in the slow wave stage of sleep, an increase of 30 minutes in the spindle stage, and a decrease of 10 minutes in the REM stage of sleep. SPA-90 is useful as an anticonvulsant, anti-anxiety, analgesic agent or sedative-hypnotic agent.

SUMMARY

SPA-4 is approximately comparable in potency to SP-7 as both an antidepressant and an anti-anxiety agent. However, SPA-4 is less potent than SP-7 as an anticonvulsant agent, and the analgesic properties have been greatly reduced or eliminated. SPA-4 is thus a more selective drug in its activity than is SP-7.

SPA-47 is comparable in potency to SP-7 as an analgesic agent. SPA-47 is somewhat less potent than SP-7 as an antidepressant, while the anticonvulsant, anti-anxiety, and antihypertensive properties have been greatly reduced or eliminated. The range of activity of SPA-47 is thus more selective than for SP-7.

SPA-90 is more potent than SP-7 in anticonvulsant, anti-anxiety, and analgesic properties. However, the antidepressant activity in SP-7 has been greatly reduced or eliminated in SPA-90 indicating a selective activity not possessed by SP-7. The sedative-hypnotic potencies of SP-7 and SPA-90 are approximately the same.

The amount of active ingredient administered may be varied; however, it is necessary that the amount of active ingredient be such that a suitable dosage is given. The selected dosage depends upon the desired therapeutic effect, on the route of administration and on the duration of treatment. Dosages of from 0.1 to 25 mg./kg. of body weight daily, preferably in divided doses, i.e., three to four times daily, can be administered.

The active agents of this invention can be administered to animals, including humans, as pure compounds. It is advisable, however, to first combine one or more of the compounds with a suitable pharmaceutical carrier to attain a satisfactory size to dosage relationship and thereby obtain a pharmaceutical composition.

Pharmaceutical carriers which are liquid or solid can be used. Solid carriers such as starch, sugar, talc and the like can be used to form powders. The powders can be used for direct administration or they may be used to make tablets or to fill gelatin capsules. Suitable lubricants like magnesium stearate, binders such as gelatin, and disintegrating agents like sodium carbonate in combination with citric acid can be used to form tablets. Sweetening and flavoring agents can also be included.

Unit dosage forms such as tablets and capsules can contain any suitable predetermined amount of one or more of the active agents, and they may be administered one or more at a time at regular intervals. Such unit dosage forms, however, should generally contain a concentration of 0.1 to 50 percent by weight of one or more of the active compounds. Unit dosage forms, such as tablets and capsules, can contain about 2 to 300 mg. of active agent.

A typical tablet can have the composition:

|  | Mg |
|---|---|
| Active agent (1) | 100 |
| Starch U.S.P. | 57 |
| Lactose U.S.P. | 73 |
| Talc. U.S.P. | 9 |
| Stearic acid | 12 |

(1) 9-hydroxy-7-(3-methyl-2-octyl)-1,4,4-trimethyl-1,2,3,4-tetrahydrocyclopenta[c] [1]benzopyran.

The compounds of this invention exhibit both oral and parenteral activity and accordingly can be formulated in dosage forms for either oral or parenteral administration to a patient.

Solid dosage forms for oral administration include capsules, tablets, pills, powders, granules and the like.

Liquid dosage forms for oral administration include emulsions, solutions, suspensions, syrups and the like, containing diluents commonly used in the art such as water. Besides inert diluents, such preparations can also include adjuvants such as wetting agents, emulsifying and suspending agents and sweetening, flavoring and perfuming agents.

Preparations for parenteral administration include sterile aqueous or non-aqueous solutions. Examples of non-aqueous solvents or vehicles are propylene glycol, polyethylene glycol, vegetable oils such as olive oil and injectable organic esters such as ethyl oleate. the parenteral preparations are sterilized by conventional methods.

The following examples are presented to further illustrate the invention.

EXAMPLE 1

9-Hydroxy-7-(3-methyl-2-octyl)-1,4,4-trimethyl-1,2,3,4-tetrahydrocyclopenta[c][1]benzopyran To 60 ml. of benzene and 4.3 ml. of phosphorous oxychloride was added 14 g. of 5-(3-methyl-2-octyl)-resorcinol and 11 g. of 5-methyl-2-carbethoxycyclopentanone [J. Org. Chem. 29, 2782 (1964)]. The solution was refluxed 13 hours and let stand at room temperture for 10 hours. Dilute sodium carbonate was then added with stirring. The reaction mixture was extracted with ether, the ether solution was dried over magnesium sulfate and then concentrated to a dark oil. The dark oil was extracted twice with pentane leaving 10.4 g. of 1-methyl-4-oxo-9-hydroxy-7-(3-methyl-2-octyl)-1,2,3,4-tetrahydrocyclopenta[c][1]benzopyran.

A methyl magnesium bromide solution was prepared by adding a solution of 175 g. of methylbromide in 450 ml. of ether dropwise to 40 g. of magnesium in 150 ml. of ether. To the solution was added 53 g. of 1-methyl-4-oxo-9-hydroxy-7-(3-methyl-2-octyl)-1,2,3,4-tetrahydrocyclopenta[c][1]benzopyran in 90 ml. of benzene and 90 ml. of ether. The mixture was refluxed for 18 hours. The mixture was cooled and then 800 ml. of saturated aqueous ammonium chloride was added very slowly. The organic phase was separated, dried over magnesium sulfate and concentrated to a residue. The residue was dissolved in 900 ml. of benzene and 0.1 g. of p-toluene-sulfonic acid was added. The mixture was refluxed for 2.5 hours, then cooled and shaken with aqueous potassium bicarbonate. The solvent was removed by evaporation. Petroleum ether and activated charcoal were added, the solution was filtered and then concentrated to give 45 g. of crude oil. The product was purified by chromatography on magnesium silicate using 95/5 petroleum ether/ether as the eluating solvent giving 25 g. of 9-hydroxy-7-(3-methyl-2-octyl)-1,4,4-trimethyl-1,2,3,4-tetrahydrocyclopenta[c][1]benzopyran.

EXAMPLE 2

9-Hydroxy-7-(3-methyl-2-octyl)-2,4,4-trimethyl-1,2,3,4-tetrahydrocyclopenta[c][1]benzopyran To 300 ml. of benzene was added 26 g. of sodium hydride with stirring under nitrogen. The sodium hydride settled and 220 ml. of benzene was withdrawn. Then 300 ml. of fresh benzene was added. The reaction mixture was refluxed and to it was added 47 g. of the diethyl ester of 3-methyladipic acid in 50 ml. of benzene dropwise. After ¼ of the ester was added, 75 ml. of benzene was distilled off at atmospheric pressure to induce reaction. The reaction then proceeded quickly. The rest of the diester was added dropwise and 150 ml. of benzene was added and the mixture was cooled in ice. After the addition of 45 ml. of acetic acid, the resulting pasty mass was treated with 100 ml. of water. The aqueous layer was extracted with benzene, dried and the combined organic layers were distilled under vacuum to give 32.1 g. of 2-carboethoxy-4-methyl cyclopentanone.

To 70 ml. of benzene was added 15 g. of 5-(3-methyl-2-octyl)-resorcinol, 14 g. of 2-carboethoxy-4-methyl cyclopentanone and 10 g. of phosphorous oxychloride followed by refluxing for 8.5 hours. After standing for 8 hours at room temperature the red solution was poured into cold dilute sodium carbonate solution and then extracted with ether. The ether layer was dried and concentrated and then triturated with pentane to give a gummy blue solid. This material was recrystallized from acetonitrile to give 7.5 g. of 2-methyl-4-oxo-9-hydroxy-7-(3-methyl-2-octyl)-1,2,3,4-tetrahydrocyclopenta[c][1]benzopyran as a light blue solid, m.p. 176°–178° C.

A solution of 45 g. of methylbromide in 180 ml. of ether was added dropwise to 10 g. of magnesium in 70 ml. of ether over a period of 40 minutes followed by refluxing for 0.5 hours. 50 ml. of ether was distilled off and to the remaining solution was added dropwise a suspension of 12.6 g. of 2-methyl-4-oxo-9-hydroxy-7-(3-methyl-2-octyl)-1,2,3,4-tetrahydrocyclopenta[c][1]benzopyran in 60 ml. of ether and 60 ml. of benzene. The mixture was refluxed for 20 hours and 250 ml. of saturated aqueous ammonium chloride was added dropwise very slowly. The reaction mixture was extracted with ether, dried over magnesium sulfate and evaporated to a residue. The residue was dissolved in 300 ml. of benzene, 0.05 g. of p-toluenesulfonic acid was added and the mixture was refluxed for 2 hours. The mixture was cooled, shaken with sodium bicarbonate, and dried over magnesium sulfate. The mixture was added to petroleum ether and treated with charcoal. After evaporation of the solvents, the residue was chromatographed using 95/5 petroleum ether/ether for elution and the product of 9-hydroxy-7-(3-methyl-2-octyl)-2,4,4-trimethyl-1,2,3,4-tetrahydrocyclopenta[c][1]benzopyran was obtained as 10.95 g. of yellow oil.

EXAMPLE 3

9-Hydroxy-7-(3-methyl-2-octyl)-2,2,4,4-tetramethyl-1,2,3,4-tetrahydrocyclopenta[c][1]benzopyran To 13.5 g. of 5-(3-methyl-2-octyl)-resorcinol and 10.5 g. of 4,4-dimethyl-2-carboethoxycyclopentanone [Canadian J. of Chem. 47, 1982-1988 (1969)] in 59 ml. of benzene was added 4.3 ml. of phosphorous oxychloride with stirring and refluxing for 6 hours. After the red solution was allowed to stand at room temperature for 8 hours, it was added to an ice and sodium carbonate solution. The colorless mixture was extracted with ether, dried over magnesium sulfate and concentrated. The mixture was extracted with cold pentane and the pentane was discarded. The residue [9-hydroxy-7-(3-methyl-2-octyl)-2,2,-dimethyl-4-oxo-1,2,3,4-tetrahydrocyclopenta[c][1]benzopyran] was obtained as a gummy solid.

22 grams of magnesium was added to 100 ml. of ether and to the mixture was added dropwise a solution of 124 g. of methyliodide in 100 ml. of ether. The mixture was refluxed for 0.5 hour and then the crude 9-hydroxy-7-(3-methyl-2-octyl)-2,2,-dimethyl-4-oxo-1,2,3,4-tetrahydrocyclopenta[c][1]benzopyran in 130 ml. of benzene was added over 20 minutes. The mixture was refluxed and stirred for 18 hours and, after cooling, 50 ml. of water was added dropwise under nitrogen. After the addition of 35 ml. of sulfuric acid and 150 ml. of water, the ether layer was separated, dried over magnesium sulfate and concentrated to a residue which was dissolved in 200 ml. of benzene. Then 250 mg. of p-toluene sulfonic acid was added followed by refluxing for 1 hour. The solvent was removed and the residue was dissolved in pentane. The solution was treated with charcoal, filtered and concentrated to 13.5 g. of 9-hydroxy-7-(3-methyl-2-octyl)-2,2,4,4-tetramethyl-1,2,3,4-tetrahydrocyclopenta[c][1]benzopyran as a dark oil. The product was purified by column chromatography to give 10.4 g. of pure product.

EXAMPLE 4

1-Ethyl-4,4-dimethyl-9-hydroxy-7-(3-methyl-2-octyl)-1,2,3,4-tetrahydrocyclopenta[c] [1]benzopyran The general procedure of Example 1 is followed in the following reactions.

2-Carboethoxycyclopentanone is reacted with ethyl iodide in the presence of sodium hydride to produce 2-carboethoxy-2-ethyl-cyclopentanone.

2-Carboethoxy-2-ethyl-cyclopentanone is reacted with sodium ethoxide to produce 5-ethyl-2-carboethoxycyclopentanone. (J. Org. Chem. 29, 2782 (1964))

5-Ethyl-2-carboethoxycyclopentanone is reacted with 5-(3-methyl-2-octyl)-resorcinol to produce 1-ethyl-4-oxo-9-hydroxy-7-(3-methyl-2-octyl)-1,2,3,4-tetrahydrocyclopenta[c] [1]benzopyran.

A solution of 40.1 g. (0.112 mole) of 1-ethyl-4-oxo-9-hydroxy-7-(3-methyl-2-octyl)-1,2,3,4-tetrahydrocyclopenta[c] [1]benzopyran in 300 ml. of ether was added dropwise to a stirred solution of 1.12 mole of methyl magnesium bromide in 340 ml. of ether. The resulting solution was stirred and refluxed for 19 hours. The reaction mixture was cooled to room temperature and to the mixture was added dropwise with stirring an ammonium chloride solution (120 g. in 350 ml. of water). The mixture was filtered to remove the inorganic salts which were well washed with benzene. The filtrate was concentrated to dryness to give a dark viscous oil which was taken up in 200 ml. of benzene. A few crystals of p-toluenesulfonic acid monohydrate were added and the mixture was refluxed 2 hours. The solvents were removed giving 1-ethyl-4,4-dimethyl-9-hydroxy-7-(3-methyl-2-octyl)-1,2,3,4-tetrahydrocyclopenta[c] [1]benzopyran as a dark viscous oil. The product was chromatographed on a magnesium silicate column and eluted with 96/4 petroleum ether/diethyl ether. After rechromatography there was obtained 8.1 g. of product. The nuclear magnetic resonance and infrared analysis of the product showed it to be the expected compound.

Analysis Calcd. for $C_{25}H_{38}O_2$: C, 81.03; H, 10.34; O, 8.63. Found: C, 80.48; H, 10.36; O, 9.4.

The foregoing detailed description has been given for clearness of understanding only, and no unnecessary limitations should be understood therefrom, as modifications will be obvious to those skilled in the art.

What is claimed is:

1. A compound of the formula

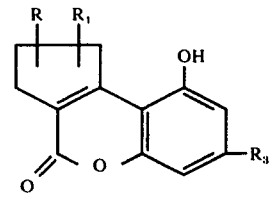

wherein R is a lower alkyl group having 1 to 5 carbons, $R_1$ is hydrogen or a lower alkyl group having 1 to 5 carbons and $R_3$ is an alkyl group having 1 to 20 carbon atoms, a phenyl-lower alkyl group or a cycloalkyl-lower alkyl group.

2. A compound according to claim 1 in which $R_3$ is an alkyl having 5 to 10 carbon atoms.

3. A compound according to claim 1 having the name 1-methyl-4-oxo-9-hydroxy-7-(3-methyl-2-octyl)-1,2,3,4-tetrahydrocyclopenta[c] [1]benzopyran.

4. A compound according to claim 1 having the name 2-methyl-4-oxo-9-hydroxy-7-(3-methyl-2-octyl)-1,2,3,4-tetrahydrocyclopenta[c] [1]benzopyran.

5. A compound having the name 9-hydroxy-7-(3-methyl-2-octyl)-2,2-dimethyl-4-oxo-1,2,3,4-tetrahydrocyclopenta[c] [1]benzopyran.

6. A compound having the name 1-ethyl-4-oxo-9-hydroxy-7-(3-methyl-2-octyl)-1,2,3,4-tetrahydrocyclopenta[c] [1]benzopyran.

* * * * *